United States Patent [19]

Schriewer et al.

[11] Patent Number: 5,237,060
[45] Date of Patent: * Aug. 17, 1993

[54] PROCESS OF PREPARING ENANTIOMERICALLY PURE 1,8-BRIDGED 4-QUINOLONE-3-CARBOXYLIC ACIDS

[75] Inventors: Michael Schriewer; Klaus Grohe, both of Odenthal; Hans-Joachim Zeiler, Velbert; Karl Metzger, Wuppertal, all of Fed. Rep. of Germany

[73] Assignee: Bayer Aktiengesellschaft, Leverkusen, Fed. Rep. of Germany

[*] Notice: The portion of the term of this patent subsequent to Aug. 22, 2006 has been disclaimed.

[21] Appl. No.: 315,372

[22] Filed: Feb. 23, 1989

Related U.S. Application Data

[62] Division of Ser. No. 939,582, Dec. 9, 1986, abandoned.

[30] Foreign Application Priority Data

Dec. 10, 1985 [DE] Fed. Rep. of Germany ....... 3543513

[51] Int. Cl.$^5$ ................. C07D 498/06; C07D 487/06
[52] U.S. Cl. .................................... 544/101; 540/547; 540/559; 544/344
[58] Field of Search ................. 544/101, 344; 540/547, 540/559

[56] References Cited

U.S. PATENT DOCUMENTS 4,762,831 8/1988 Grohe et al. ................. 544/101
4,777,253 10/1988 Mitscher et al. ............. 544/101
4,859,773 8/1989 Grohe et al. ................. 544/101

FOREIGN PATENT DOCUMENTS 0047005 3/1982 European Pat. Off. .

Primary Examiner—Richard L. Raymond
Attorney, Agent, or Firm—Sprung Horn Kramer & Woods

[57] ABSTRACT

The invention relates to a process for the preparation of highly antibacterially active enantiomerically pure 1,8-bridged 4-quinolone-3-carboxylic acids and derivatives of the formula (I)

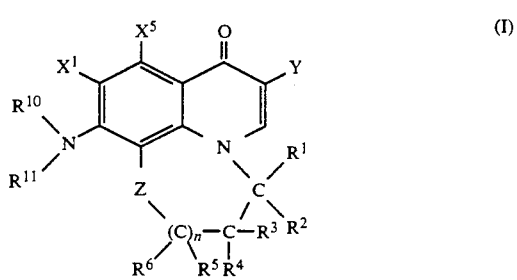

in which
1) a compound of the formula

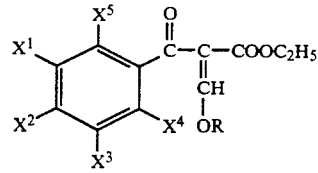

is reacted with a compound of the formula

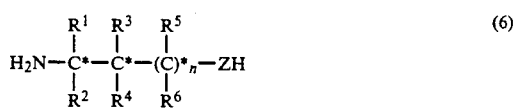

(6)

to form a compound of the formula

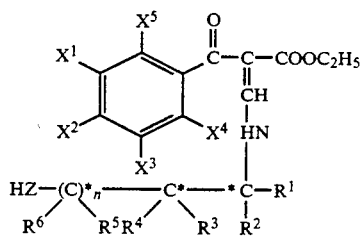

followed by cyclization to form a compound of the formula

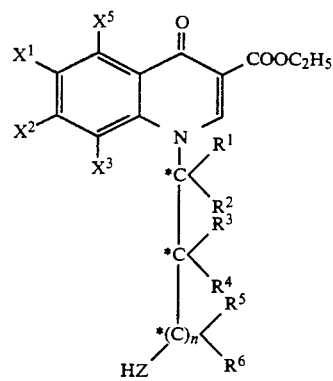

and further cyclization to form a compound of the formula

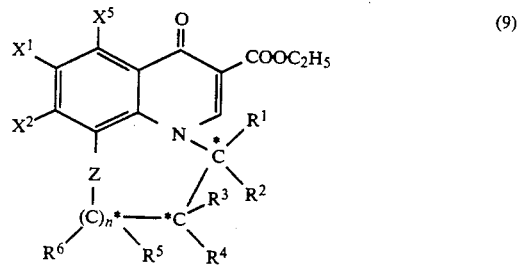

(9)

an finally reaction of the cyclized product with amines of the formula

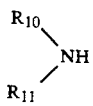

3 Claims, No Drawings

PROCESS OF PREPARING ENANTIOMERICALLY PURE 1,8-BRIDGED 4-QUINOLONE-3-CARBOXYLIC ACIDS

This is a division of application Ser. No. 939,582, filed Dec. 9, 1986, now abandoned.

The invention relates to enantiomerically pure 1,8-bridged 4-quinolone-3-carboxylic acids, a process for their preparation and their use as medicaments, in particular as antibacterial agents in human and veterinary medicine.

The invention relates to highly antibacterially active enantiomerically pure 1,8-bridged 4-quinoline-3-carboxylic acids and derivatives of the formula (I)

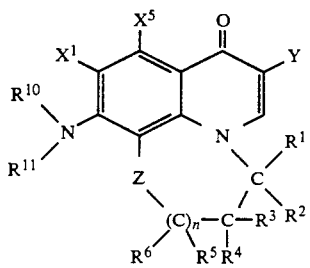

in which

Y represents a carboxyl group, a nitrile group, an ester group —COOR$^7$ or an acid amide group —CONR$^8$R$^9$, wherein R$^7$ represents C$_1$–C$_4$-alkyl and R$^8$ and R$^9$ represent hydrogen or C$_1$–C$_4$-alkyl, and R$^9$ can also be optionally substituted phenyl, X$^1$ represents hydrogen, nitro, alkyl with 1 to 3 carbon atoms or halogen, preferably fluorine, X$^5$ can be hydrogen, halogen or methyl, R$^{10}$ and R$^{11}$, together with the nitrogen atom to which they are bonded, form a 5- or 6-membered heterocyclic ring which can additionally contain, as a ring member, the atoms of groups —O—, —S—, —SO—, —SO$_2$—,

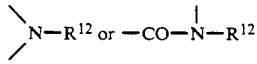

and which can optionally be mono-, di- or trisubstituted on the carbon atoms by C$_1$–C$_4$-alkyl, by phenyl or cyclohexyl which is optionally mono-, di- or trisubstituted by chlorine, fluorine, bromine, methyl, phenyl, hydroxyl, methoxy, benzyloxy, nitro or piperidino, or by 2-thienyl, hydroxyl, alkoxy with 1 to 3 carbon atoms, amino, methylamino, ethylamino, aminomethyl, methylaminomethyl or ethylaminomethyl, wherein R$^{12}$ represents hydrogen or a branched or straight-chain alkyl, alkenyl or alkinyl group which has 1 to 6 carbon atoms and can optionally be substituted by one or two hydroxyl, alkoxy, alkylamino or dialkylamino groups with 1 to 3 carbon atoms in each alkyl radical, the cyano group or thee alkoxy carbonyl group with 1 to 4 carbon atoms in the alkoxy part, or represents a phenylalkyl group which has up to 4 carbon atoms in the alkyl part and is optionally substituted in the phenyl radical, a phenacyl radical which is optionally mono- or disubstituted by hydroxyl, methoxy, chlorine or fluorine, or an oxoalkyl radical with up to 6 carbon atoms, or furthermore denotes a radical COR$^{13}$ or SO$_2$R$^{14}$, wherein R$^{13}$ represents hydrogen or straight-chain or branched alkyl which has 1 to 4 carbon atoms and is optionally substituted by 1 or 2 substituents from the series comprising amino, alkoxycarbonyl with 1 to 3 carbon atoms in the alkoxy part, carboxyl, alkoxy with 1 to 3 carbon atoms and halogen, such as chlorine, bromine or fluorine, or represents alkoxy with 1 to 4 carbon atoms, amino or alkylamino or dialkylamino with 1 to 5 carbon atoms in the alkyl part and R$^{14}$ represents straight-chain or branched alkyl with 1 to 3 carbon atoms, and Z represents oxygen or an amine radical NR$^{15}$, wherein R$^{15}$ denotes hydrogen or an alkyl radical which has 1–6 carbon atoms and is optionally substituted by halogen, trifluoromethyl, nitro, cyano, hydroxyl, alkoxy or alkylmercapto with 1–3 carbon atoms, aryloxy, arylthio or an ester radical with 1–3 carbon atoms in the alcohol part, or denotes a phenyl radical which is optionally substituted by halogen, a nitro group, an alkyl group with 1–3 carbon atoms or an alkoxy or alkylmercapto group with in each case 1–3 carbon atoms, or furthermore represents an acyl radical R$^{16}$—CO— or R$^{17}$SO$_2$—, wherein R$^{16}$ and R$^{17}$ represents alkyl radicals with 1–6 carbon atoms or optionally substituted phenyl radicals, or can be a

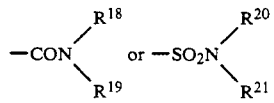

radical, wherein the radicals R$^{18}$ to R$^{21}$ represent hydrogen, alkyl with 1–6 carbon atoms or an optionally substituted phenyl radical, and R$^1$, R$^2$, R$^3$, R$^4$, R$^5$ and R$^6$ represent hydrogen or an alkyl group which has 1–6 carbon atoms and is optionally mono- or polysubstituted by halogen, in particular chlorine or fluorine, and furthermore nitro, cyano, hydroxyl, alkoxy or alkylmercapto with 1–3 carbon atoms in the alkyl part, or represent a phenyl radical, naphthyl radical or heterocyclic radical, such as, for example, a thiophene, furan, pyrrole, thiazole, pyridine or pyrimidine radical, which is optionally substituted by halogen, nitro, alkyl or alkoxy or alkylmercapto with in each case up to 3 carbon atoms, hydroxyl, aryloxy, arylthio, cyano or an ester radical with 1–3 carbon atoms in the alcohol part, with the proviso that R$^1$ and R$^2$ and/or R$^3$ and R$^4$ and/or R$^5$ and R$^6$ are different, and R$^2$ with R$^3$ and/or R$^4$ with R$^5$, in each case with the carbon atoms to which they are bonded, form a 3- to 7-membered ring which is optionally substituted by optionally substituted alkyl radicals with 1–3 carbon atoms or optionally substituted aryl radicals and n denotes 0 or 1, and pharmaceutically usable hydrates and alkali metal, alkaline earth metal, silver and guanidinium salts thereof, and their esters.

They are therefore suitable as active compounds for human and veterinary medicine, and above all as intermediate products for such bactericides.

Preferred compounds of the formula (I) are those in which

Y represents a carboxyl group, a nitrile group or an ester group —COOR$^7$, wherein R$^7$ can be methyl or ethyl, X$^1$ represents fluorine, X$^5$ represents hydrogen, R$^{10}$ and R$^{11}$, together with the nitrogen atom to which they are bonded, can form a 5- or 6-membered heterocyclic ring which can additionally contain, as a ring member, an oxygen atom or the groups

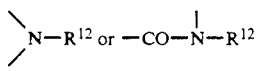

and which can optionally be mono- or disubstituted on the carbon atoms by C$_1$-C$_2$-alkyl, cyclohexyl or phenyl which is optionally substituted by chlorine, fluorine, methyl, phenyl, hydroxyl, methoxy, benzyloxy, nitro or piperidino, or by 2-thienyl or hydroxyl, wherein R$^{12}$ represent hydrogen or a branched or straight-chain alkyl group which has 1 to 3 carbon atoms and can optionally be substituted by one or two hydroxyl groups, or represents a phenacyl radical, or an oxalkyl radical with up to 4 carbon atoms, or a radical COR$^{13}$, wherein R$^{13}$ denotes hydrogen or alkyl with one or two carbon atoms, Z represents oxygen or an amine radical NR$^{15}$, wherein R$^{15}$ represents an alkyl radical with 1–4 carbon atoms or represents a phenyl radical which is optionally substituted by halogen, methyl or nitro, and, if n=0 or n=1, the abovementioned definitions apply to R$^1$-R$^6$.

It has furthermore been found that the compounds of the formula (I) are obtained by a process in which enantiomerically pure quinolonecarboxylic acid derivatives of the formula (II)

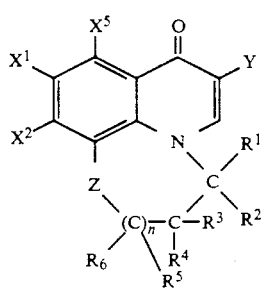

in which the radicals X$^1$, X$^5$, R$^1$-R$^6$, Z, Y and n have the abovementioned meaning and X$^2$ preferably represents chlorine or fluorine, are reacted with amines of the formula (III)

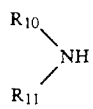

in which

R$_{10}$ and R$_{11}$ have the abovementioned meaning, if appropriate in the presence of acid-binding agents (method A).

This process does not necessarily have to be carried out in such a manner that R$^{10}$ and R$^{11}$ in the amines of the formula III already have the final meaning which they have in the compounds of the formula (I) according to the invention. It is indeed also possible to use precursors of the radicals R$^{10}$ and R$^{11}$ in a first step which are then converted into the final form of R$^{10}$ and R$^{11}$ in one or more subsequent reaction steps. Thus, for example, it is also possible to obtain compounds of the formula (I) according to the invention by reacting an enantiomerically pure 10-(1-piperazinyl) compound (when n=0) or an enantiomerically pure 11-(1-piperazinyl) compound (when n=1) of the formula (IV).

Compounds of the formula (I) according to the invention can, for instance, also be obtained by a process in which an enantiomerically pure 10-(1-piperazinyl) compound (for n=0) or enantiomerically pure 11-(1-piperazinyl) compound (for n=1) of the formula (IV)

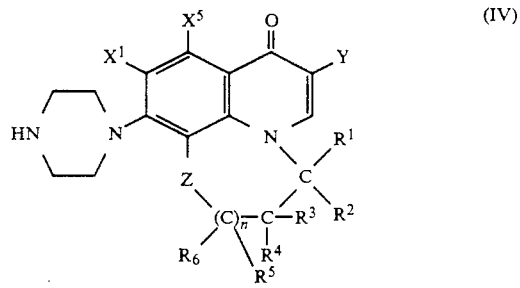

in which

X$^1$, X$^5$, R$^1$-R$^6$, Z, Y and n have the abovementioned meaning, and the piperazinyl radical can be mono-, di- or trisubstituted on the carbon atoms in the manner mentioned under R$^{10}$ and R$^{11}$, for instance, by C$_1$-C$_4$-alkyl, 2-thienyl or optionally substituted cyclohexyl or phenyl, are reacted with compounds of the formula (V)

in which

R$^{12}$ has the abovementioned meaning, but cannot be hydrogen, and

X denotes fluorine, chlorine, bromine, iodine, hydroxyl, acyloxy, ethoxy, phenoxy or 4-nitrophenoxy, if appropriate in the presence of acid-binding agents (method B).

Thus in this reaction procedure the piperazinyl radical located in the 10- or 11-position can be introduced in a first reaction step by thee method mentioned first—which produces the compound IV already forming part of the invention—and then in a subsequent step other substituents which may be required can be introduced such as, in this case, R$^{12}$.

In a further embodiment the compounds of the formula (I) according to the invention are also obtained by a process in which enantiomerically pure 10-(1-piperazinyl)quinolonecarboxylic acid derivatives (n=0) or enantiomerically pure 11-(1-piperazinyl)-quinolonecarboxylic acid derivatives (n=1) of the formula (IV) in which the piperazinyl radical can be mono-, di- or trisubstituted on the carbon atoms by $C_1$–$C_4$-alkyl, 2-thienyl or optionally substituted cyclohexyl or phenyl, are reacted with Michael acceptors of the formula (VI)

$$B-CH=CH_2 \quad (VI)$$

in which

B represents CN, CO—$R^{22}$ or COO$R^{23}$, wherein $R^{22}$ represents methyl or ethyl and $R^{23}$ represents methyl, ethyl or n- or 1-propyl (method C).

If 1-methylpiperazine and enantiomerically pure 9,10-difluoro-2,3-dihydro-7-oxo-2-phenyl-7H-pyrido [1,2,3-de][1,4]benzoxazine-6-carboxylic acid is used as the starting substances in the reaction according to method A, the course of the reaction can be represented by the following equation:

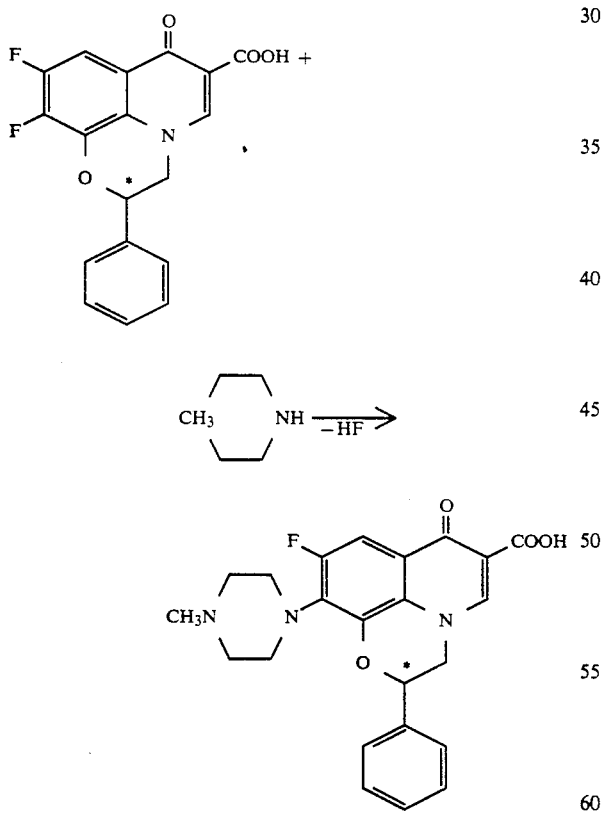

If ethyl iodide and enantiomerically pure 9-fluoro-2,3-dihydro-7-oxo-2-phenyl-10(1-piperazinyl)-7H-pyrido[1,2,4-de][1,4]benzoxazine-carboxylic acid are used as starting substances in the reaction according to method B, the course of the reaction can be represented by the following equation:

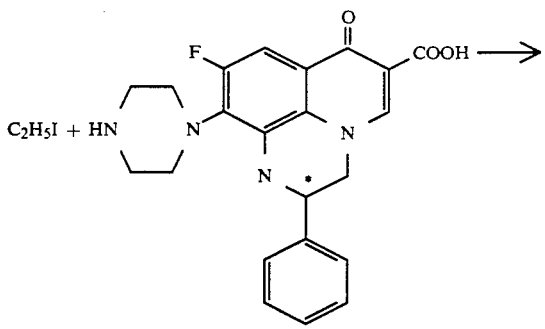

If, for example, enantiomerically pure 9-fluoro-2,3-dihydro-7-oxo-2-phenyl-10(1-piperazinyl)-7H-pyrido-[1,2,3][1,4]benzoxazine-6-carboxylic acid and methyl vinyl ketone are used as starting substances according to method C, the course of the reaction can be represented by the following equation:

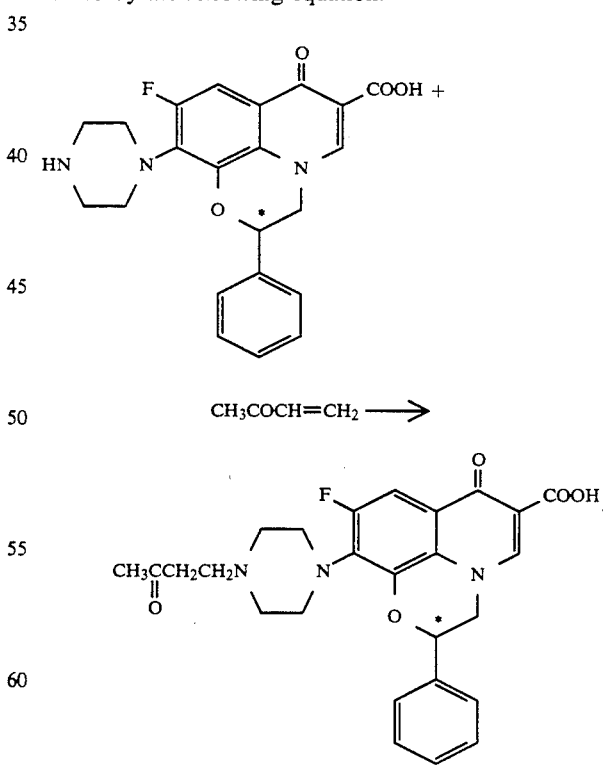

The quinolonecarboxylic acids of the formula (II) which can be used as starting substances according to method A can be prepared in accordance with the following equation:

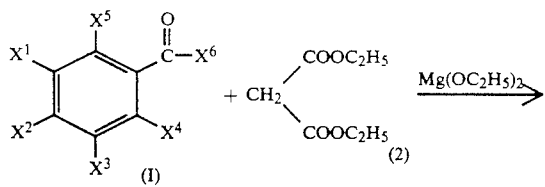
$X^3 = X^4 = F, Cl, NO_2 \qquad X^6 = Cl, Br, F$
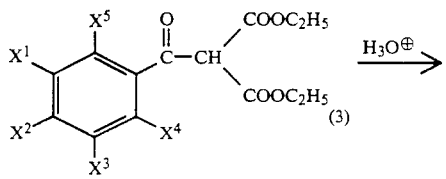
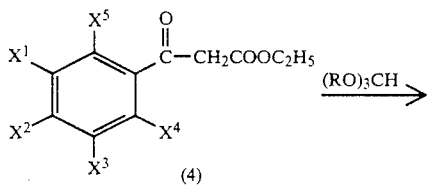
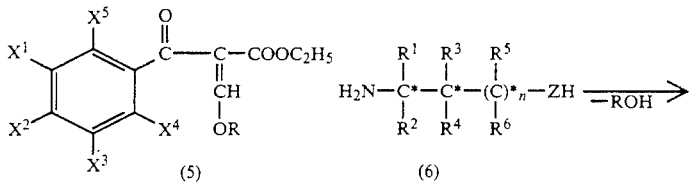
$R = CH_3, C_2H_5$ or $C_3H_7$-n
*where appropriate, optically active centre
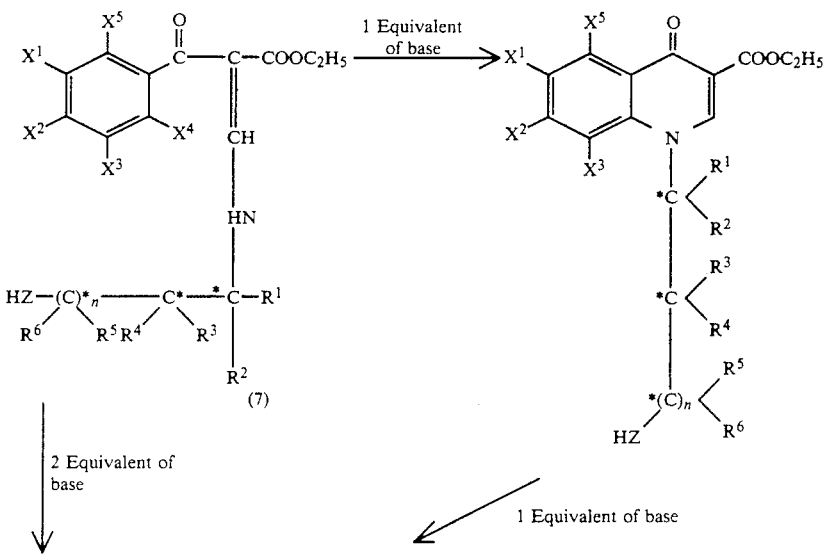

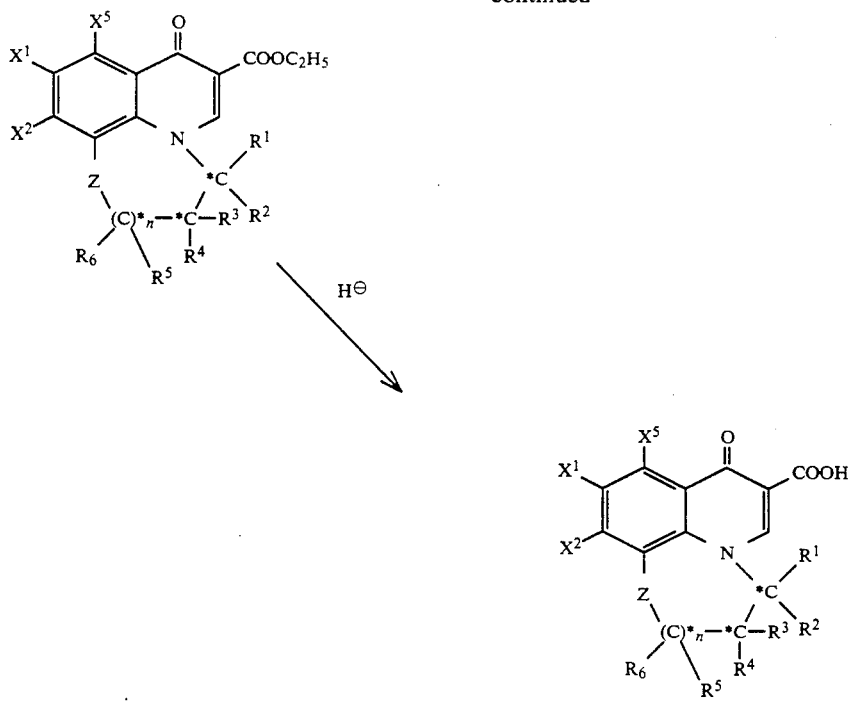

*where appropriate, optically active centre

According to this reaction, diethyl malonate (2) is acylated in the presence of magnesium ethylate with the corresponding benzoyl fluoride or chloride (1) to give the benzoyl malonate (3) (Organicum, 3rd edition 1964, page 438).

Partial hydrolysis and decarboxylation of (3) in an aqueous medium with catalytic amounts of sulphuric acid or p-toluenesulphonic acid gives a good yield of the ethyl benzoylacetate (4), which is converted into the ethyl 3-ethoxyacrylate (5) with triethyl orthoformate/acetic anhydride. The reaction of (5) with the corresponding amine (6) in a solvent, such as, for example, methylene chloride, alcohol, chloroform, cyclohexane or toluene, leads to the desired intermediate product (7) in a slightly exothermic reaction.

The cyclization reactions (7)→(9) or (8)→(9) are carried out in a temperature range from about 60° to 300° C., preferably 80° to 180° C.

Dioxane, dimethylsulphoxide, N-methylpyrrolidone, sulpholane, hexamethylphosphoric acid triamide and, preferably, N,N-dimethylformamide can be used as diluents.

Possible acid-binding agents for this reaction stage are potassium tert.-butanolate, butyl-lithium, lithium phenyl, phenylmagnesium bromide, sodium methylate, sodium hydride, sodium carbonate or potassium carbonate and particularly preferably potassium fluoride or sodium fluoride.

In general, in each case one equivalent of base is used for the primary cyclization (7)→(8) and the second cyclization (8)→(9).

If the two cyclization reactions are combined in a "one-pot reaction" (7)→(9), 2 equivalents of the above-mentioned bases must be employed. It may be advantageous for an excess of about 10 mol % of base to be employed in the cyclocondensations (7)→(9) and (8)→(9).

The hydrolysis of the esters (9) carried out in the last step to give the corresponding carboxylic acids can be carried out under the customary known acid or basic conditions.

The 2,3,4,5-tetrafluorobenzoyl chloride used as the starting substances for this synthesis route and the pentafluorobenzoyl chloride are known.

3,5-Dichloro-2,4-difluoro-benzoyl fluoride (boiling point 97°/29 mbar; $n^{20} = 1.5148$) and 5-chloro-2,3,4-trifluoro-benzoyl fluoride (boiling point 66°-70°/20 mbar; $n^{20} = 1.4764$) are obtained side by side when tetrachlorobenzoyl chloride is heated at elevated temperatures with potassium fluoride in sulpholane:

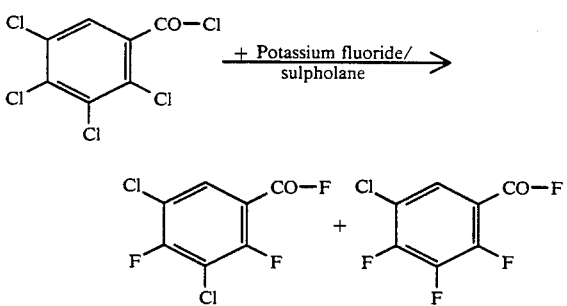

Chlorination of 2,4,5-trifluorobenzoic acid in chlorosulphonic acid leads to 3-chloro-2,4,5-trifluorobenzoic acid, which is reacted as a crude product with thionyl chloride to give 3-chloro-2,4,5-trifluorobenzoyl chloride (boiling point 94°/18 mbar; $n_D^{20} = 1.5164$):

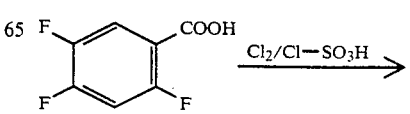

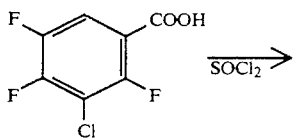

2,4-Dichloro-5-fluoro-3-nitro-benzoyl chloride is obtained by nitration of 2,4-dichloro-5-fluoro-benzoic acid, which is known, to give 2,4-dichloro-5-fluoro-3-nitro-benzoic acid and reaction thereof with thionyl chloride.

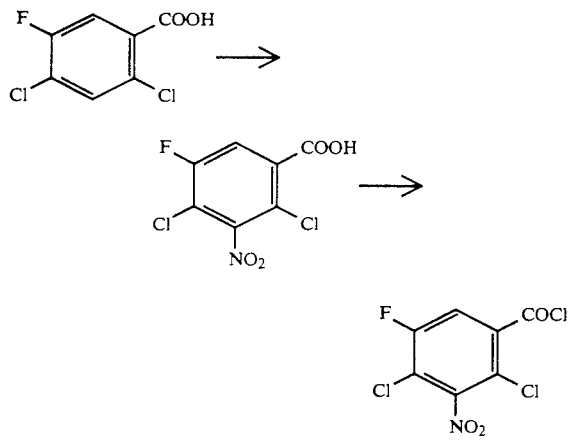

The enantiomerically pure amines of the formula (6) used as starting substances are known. Examples which may be mentioned are: D-2-amino-butanol, L-2-amino-butanol, D-2-amino-3-methyl-butanol, L-2-amino-3-methyl-butanol, D-2-amino-3-phenyl-propanol, L-2-amino-3-phenyl-propanol, D-2-amino-2-phenyl-ethanol, L-2-amino-2-phenyl-ethanol, D-1-amino-2-propanol, L-1-amino-2-propanol, D-1,2-diamino-propane, L-1,2-diamino-propane, L-1,3-diamino-butane and D-1,3-diamino-butane.

The amines (III) used as starting substances are known or can be obtained by processes which are known from the literature [U.S. Pat. No. 4,166,180 and J. Med. Chem. 26, 1116 (1983)]. Catalytic hydrogenation of the 2-aryl-piperazines gives the corresponding 2-cyclohexyl-piperazines: for example: 2-cyclohexyl-piperazine (waxy, melting point 71°-73° C.). Examples which may be mentioned are: morpholine, piperidine, thiomorpholine, pyrrolidone, piperazine, N-methylpiperazine, N-ethylpiperazine, N-(2-hydroxyethyl)piperazine, N-formylpiperazine, 2-methylpiperazine, 1,2-dimethylpiperazine, cis- and trans-2,5-dimethyl-piperazine, 1-ethylpiperazine, 2-propylpiperazine, 2-isopropylpiperazine, 2-isobutylpiperazine, 2-piperazinone, 1-methyl-2-piperazinone, 1-ethyl-2-piperazinone, 2-cyclohexyl-piperazine, 2-phenylpiperazine, 2-(4-chloro-phenyl)-piperazine, 2-(4-fluorophenyl)-piperazine, 2-(4-bromo-phenyl)-piperazine, 2-(4-methylphenyl)-piperazine, 2-(4-biphenyl)-piperazine, 2-(4-methoxyphenyl)-piperazine, 2-(4-benzyloxyphenyl)-piperazine, 2-(4-hydroxyphenyl)-piperazine, 2-(4-nitrophenyl)-piperazine, 2-(3-nitrophenyl)-piperazine, 2-(4-piperidino-phenyl)-piperazine, 2-(3,4-dimethoxyphenyl)-piperazine, 2-(3,4,5-trimethoxyphenyl)-piperazine, 2-(3,4-dimethoxy-6-methyl)-piperazine, 2-(2-thienyl)-piperazine and 3-amino-pyrrolidine.

The compounds of the formula (V) used as starting substances are known. Examples which may be mentioned are: methyl iodide, methyl bromide, ethyl iodide, ethyl bromide, ethyl chloride, 2-hydroxyethyl chloride, 3-hydroxypropyl chloride, 4-hydroxybutyl chloride, n-propyl bromide, i-propyl iodide, n-butyl bromide, i-butyl bromide, sec.-butyl chloride, n-pentyl chloride, 3-methylbutyl chloride and n-hexyl bromide.

Formic acetic anhydride, acetic anhydride, propionic anhydride, acetyl chloride, chloroacetyl chloride, dichloroacetyl chloride, bromoacetyl bromide, butyryl chloride, 4-chlorobutyryl chloride, isobutyryl chloride, N-(tert.-butoxycarbonyl)glycine 4-nitrophenyl ester, N-(tert.-butoxycarbonyl)-L-alanine 4-nitro-phenyl ester, N-(tert.-butoxycarbonyl)-L-leucine 4-nitro-phenyl ester, N-(tert.-butoxycarbonyl)-L-valine 4-nitrophenyl ester, 3-methoxypropionyl chloride, methyl chlorocarbonate, ethyl chlorocarbonate, n-butyl chlorocarbonate, diethyl carbonate, cyanogen chloride, diphenyl carbonate, cyanogen bromide, dimethylcarbamyl chloride, methanesulphonyl chloride, ethanesulphonyl chloride, propane-1-sulphonyl chloride and formic acid.

The compounds of the formula (VII) which can be used according to the invention are known. Examples which may be mentioned are: acrylonitrile, methyl vinyl ketone, methyl acrylate and ethyl acrylate.

The reaction of (II) with (III) according to method A is preferably carried out in a diluent, such as dimethylsulphoxide, N,N-dimethylformamide, hexamethylphosphoric acid triamide, sulpholane, water, an alcohol, such as methanol, ethanol, n-propanol, isopropanol or glycol monomethyl ether, or pyridine. Mixtures of these diluents can likewise be used.

Acid-binding agents which can be used are all the customary inorganic and organic acid-binding agents. These include, preferably, the alkali metal hydroxides, alkali metal carbonates, organic amines and amidines. Acid-binding agents which may be mentioned specifically as being particularly suitable are: triethylamine, 1,4-diaza-bicyclo[2,2,2]-octane (DABCO), 1,8-diazabicyclo[5,4,0]-undec-7-ene (DBU) or excess amine (III).

The reaction temperatures can be varied within a substantial range. The reaction is in general carried out between about 20° and 200° C., preferably between 80° and 180° C.

The reaction can be carried out under normal pressure, but also under increased pressure. It is in general carried out under pressures between about 1 and about 100 bar, preferably between 1 and 10 bar.

In carrying out the process according to the invention, 1 to 15 mol, preferably 1 to 6 mol, of the amine (III) are employed per mol of the carboxylic acid (II).

The reaction of (IV) with (V) is preferably carried out in a diluent, such as dimethylsulphoxide, dioxane, N,N-dimethylformamide, hexamethyl-phosphoric acid trisamide, sulpholane, water, an alcohol, such as methanol, ethanol, n-propanol, isopropanol or glycol monomethyl ether, or pyridine. Mixtures of these diluents can likewise be used.

All the customary inorganic and organic acid-binding agents can be used as the acid-binding agents. These include, preferably, the alkali metal hydroxides, alkali metal carbonates, organic amines and amidines. Acid-binding agents which may be mentioned specifically as being particularly suitable are: triethylamine, 1,4-diazabicyclo[2,2,2]octane (DABCO) or 1,8-diazabicyclo [5,4,0]undec-7-ene (DBU).

The reaction temperatures can be varied within a substantial range. The reaction is in general carried out between about 20° and about 180° C., preferably between 40° and 110° C.

The reaction can be carried out under normal pressure, but also under increased pressure. It is in general carried out under pressures between about 1 and about 100 bar, preferably between 1 and 10 bar.

In carrying out the process according to the invention by method B, 1 to 4 mol, preferably 1 to 1.5 mol, of the compound (V) are employed per mol of the compound (IV).

The reaction of (IV) with (VI) (method C) is preferably carried out in a diluent, such as dioxane, dimethylsulphoxide, N,N-dimethylformamide, methanol, ethanol, isopropanol, n-propanol or glycol monomethyl ether, or in mixtures of these diluents.

The reaction temperatures can be varied within a substantial range. The reaction is in general carried out between about 20° C. and about 150° C., preferably between 50° C. and 100° C.

The reaction can be carried out under normal pressure, but also under increased pressure. It is in general carried out under pressures between about 1 and about 100 bar, preferably between 1 and 10 bar.

In carrying out the process according to the invention by method C, 1 to 5 mol, preferably 1 to 2 mol, of the compound (VI) are employed per mol of the compound (IV).

New active compounds which may be mentioned specifically, in addition to the compounds listed in the examples, are: 2R-9-fluoro-2-fluoromethyl-2,3-dihydro-7-oxo-10(1-pyrrolidinyl)-7H-pyrido[1,2,3]benzoxazine-6-carboxylic acid, 2R-9-chloro-2,3-dihydro-2-hydroxymethyl-10(4-methyl-1-piperazinyl)-7-oxo-7H-pyrido[1,2,3-de][1,4]-benzoxazine-6-carboxylic acid, 2R-9-fluoro-2,3-dihydro-2-hydroxymethyl-10(4-methyl-1-piperazinyl)-7-oxo-7H-pyrido-[1,2,3-de][1,4]-benzoxazine-6-carboxylic acid, 2S-9-fluoro-2,3-dihydro-7-oxo-2-phenyl-10-(1-pyrrolidinyl)-7H-pyrido[1,2,3-de][1,4]-benzoxazine-6-carboxylic acid, 2S-9-chloro-2,3-dihydro-7-oxo-2-phenyl-10-(1-pyrrolidinyl)-7H-pyrido[1,2,3-de][1,4]-benzoxazine-6-carboxylic acid, 3S-9-fluoro-2,3-dihydro-2,2-dimethyl-3-methyl-10-(4-methyl-1-piperazinyl)-7-oxo-7H-pyrido[1,2,3-de][1,4]-benzoxazine-6-carboxylic acid, 2R-9-fluoro-2,3-dihydro-2-methyl-3,3-dimethyl-10-(4-methyl-1-piperazinyl)-7-oxo-7H-pyrido[1,2,3-de][1,4]-benzoxazine-6-carboxylic acid, 3aR, 11aS-6-fluoro-3a,11a-dihydro-8-oxo-5-(1-pyrrolidinyl)-8H-cyclopenta[1,2-b]-pyrido[1,2,3-de][1,4]-benzoxazine-9-carboxylic acid, 3aR, 11aS-6-chloro-3a,11a-dihydro-8-oxo-5-(1-pyrrolidinyl)-8H-cyclopenta[1,2-b]-pyrido[1,2,3-de][1,4]-benzoxazine-9-carboxylic acid, 3aR, 11aS-6-fluoro-3a, 11a-dihydro-8-oxo-5(3-phenyl-1-piperazinyl)-8H-cyclopenta[1,2-b]-pyrido[1,2,3-de][1,4]-benzoxazine-9-carboxylic acid, 3S-9-fluoro-2,3-dihydro-3-methyl-10(4-methyl-1-piperazinyl)-7-oxo-1H; 7H-pyrido[1,2,3-de]-quinoxaline-6-carboxylic acid, 3S-9-fluoro-2,3-dihydro-3-methyl-7-oxo-10(-1-piperazinyl)-1H,7H-pyrido[1,2,3-de]-quinoxaline-6-carboxylic acid, 3S-9-fluoro-2,3-dihydro-1,3-dimethyl-10(4-methyl-1-piperazinyl)-7-oxo-7H-pyrido[1,2,3-de]-quinoxaline-6-carboxylic acid, 3S-9-fluoro-2,3-dihydro-1,3-dimethyl-10(3-methyl-1-piperazinyl)-7-oxo-7H-pyrido[1,2,3-de]-quinoxaline-6-carboxylic acid, 2R-9-fluoro-2,3-dihydro-1,2-dimethyl-10-(4-methyl-1-piperazinyl)-7-oxo-7H-pyrido[1,2,3-de]-quinoxaline-6-carboxylic acid, 2R-9-fluoro-2,3-dihydro-3-methyl-10(4-methyl-1-piperazinyl)-7-oxo-2-phenyl-7H-pyrido[1,2,3-de]-quinoxaline-6-carboxylic acid, 4S-10-fluoro-2,3-dihydro-4-methyl-11(4-methyl-1-piperazinyl)-8-oxo-4H, 8H-pyrido[1,2,3-ef][1,5]-benzoxazepine-7-carboxylic acid, 4S-10-fluoro-2,3-dihydro-4-methyl-11(3-methyl-1-piperazinyl)-8-oxo-4H, 8H-pyrido[1,2,3-ef][1,5]-benzoxazepine-7-carboxylic acid, 4S-10-fluoro-2,3-dihydro-4-methyl-8-oxo-11-(1-pyrrolidinyl)-4H, 8H-pyrido[1,2,3-ef][1,5]-benzoxaxzepine-7-carboxylic acid, 3R-10-chloro-2,3-dihydro-3-methyl-11(4-methyl-1-piperazinyl)-8-oxo-4H, 8H-pyrido[1,2,3-ef][1,4]-benzoxazepine-7-carboxylic acid, 4aR, 12aS-7-fluoro-4-a, 12a-dihydro-9-oxo-6(1-piperazinyl)-9H-cyclohexa[1,2-b]-pyrido [1,2,3-de][1,4]-benzoxazine-10-carboxylic acid, 4aR, 12aS-7-chloro-4a, 12a-dihydro-9-oxo-6(1-pyrrolidinyl)-9H-cyclohexa[1,2-b]-pyrido[1,2,3-de][1,4]-benzoxazine-10-carboxylic acid and 4aR, 12aS-7-fluoro-4a, 12a-dihydro-6-(4-methyl-1-piperazinyl)-9-oxo-9H-cyclohexa-[1,2-b]-pyrido[1,2,3-de][1,4]-benzoxazine-10-carboxylic acid.

EXAMPLE OF A TABLET ACCORDING TO THE INVENTION

Each tablet contains:

| | |
|---|---|
| Compound of Example 4 | 583.0 mg |
| Microcrystalline cellulose | 55.0 mg |
| Maize starch | 72.0 mg |
| Insoluble poly-(1-vinyl-2-pyrrolidone) | 30.0 mg |
| Highly disperse silicon dioxide | 5.0 mg |
| Magnesium stearate | 5.0 mg |
| | 750.0 mg |
| Poly-(0-hydroxypropyl-0-methyl)-cellulose 15 cp | 6.0 mg |
| Macrogol 4000 recommended INN polyethylene glycol (DAB) | 2.0 mg |
| Titanium (IV) oxide | 2.0 mg |
| | 10.0 mg |

The enantiomerically pure compounds according to the invention show, in the customary concentrations, better actions than the racemates obtained in the customary preparation methods for 1,8-bridged quinolone-carboxylic acids.

Due to the smaller amounts used and the absence of inactive enantiomers, the compounds according to the invention are far superior to conventional 1,8-bridged quinolonecarboxylic acids which are present as racemates.

The compounds according to the invention exhibit a broad antibacterial spectrum against Gram-positive and Gram-negative germs, in particular against Enterobacteriaceae; above all against those which are resistant towards various antibiotics, such as, for example, penicillins, cephalosporins, aminoglycosides, sulphonamides and tetracyclines, coupled with a low toxicity.

These useful properties enable them to be used as chemotherapeutic active compounds in medicine and as substances for preserving inorganic and organic materials, in particular all types of organic materials, for example polymers, lubricants, paints, fibres, leather, paper and wood, and foodstuffs and water.

The compounds according to the invention are active against a very broad spectrum of microorganisms. With their aid it is possible to combat Gram-negative and Gram-positive bacteria and bacteria-like microorganisms and to prevent, alleviate and/or cure the diseases caused by these pathogens.

The compounds according to the invention are particularly active against bacteria and bacteria-like microorganisms. They are therefore particularly suitable in human and veterinary medicine for the prophylaxis and chemotherapy of local and systemic infections caused by the pathogens.

For example, local and/or systemic diseases which are caused by the following pathogens or by mixtures of the following pathogens can be treated and/or prevented: Gram-positive cocci, for example Staphylococci (*Staph. aureus* and *Staph. epidermidis*) and Streptococci (*Strept. agalactiae, Strept. faecalis, Strept. pneumoniae* and *Strept. pyogenes*); Gram-negative cocci (*Neisseria gonorrhoeae*) and Gram-negative rod-shaped bacillae, such as Enterobacteriaceae, for example *Escherichia coli, Hoemophilus influenzae,* Citrobacter (*Cibrob. freundii* and *Citrob. divernis*), Salmonella and shigella; and furthermore Klebsiellae (*Klebs. pneumoniae* and *Klebs. oxytoca*), Enterobacter (*Ent. aerogenes* and *Ent. agglomerans*), Hafnia, Serratia (*Serr. marcescens*), Proteus (*Pr. mirabilis, Pr. rettgeri* and *Pr. vulgaris*), Providencia, Yersinia and the genus Acinetobacter. The antibacterial spectrum moreover includes the genus Pseudomonas (*Ps. aeruginosa* and *Ps. maltophilia*) as well as strictly anaerobic bacteria, such as, for example, Bacteroides fragilis, representatives of the genus Peptococcus, Peptostreptococcus and the genus Clostridium; and furthermore Mycoplasma (*M. pneumoniae, M. hominis* and *M. urealyticum*) and Mycobacteria, for example Mycobacterium tuberculosis.

The above list of pathogens is purely by way of example and is in no way to be interpreted as limiting. Examples which may be mentioned of diseases which are caused by the pathogens or mixed infections and which can be prevented, alleviated or cured by the compounds according to the invention are: infectious diseases in humans, such as, for example, otitis, pharyngitis, pneumonia, peritonitis, pyelonephritis, cystitis, endocarditis, systemic infections, bronchitis (acute and chronic), septic infections, diseases of the upper respiratory tract, diffuse panbronchiolitis, pulmonary emphysema, dysentery, enteritis, liver abscesses, urethritis, prostatitis, epididymitis, gastrointestinal infections, bone and joint infections, cystic fibrosis, skin infections, postoperative wound infections, abscesses, phlegmons, wound infections, infected burns, burn wounds, infections in the oral regions, infections following dental operations, osteomyelitis, septic arthritis, cholecystitis, peritonitis with appendicitis, cholangitis, intraaodiminal abscesses, pancreatitis, sinusitis, mastoiditis, mastitis, tonsillitis, typhoid fever, meningitis and infections of the nervous system, salpingitis, endometritis, genital infections, pelveoperintonitis and eye infections.

Apart from in humans, bacterial infections can also be treated in other species. Examples which may be mentioned are: pigs: coli diarrhoea, enterotoxaemia, sepsis, dysentery, salmonellosis, metritis-mastitisagalactiae syndrome and mastitis; ruminants (cattle, sheep, goats): diarrhoea, sepsis, bronchopneumonia, salmonellosis, pasteurellosis, mycoplasmosis and genital infections; horses: bronchopneumonia, joint ill, puerperal and post-puerperal infections and salmonellosis; dogs and cats: bronchopneumonia, diarrhoea, dermatitis, otitis, urinary tract infections and prostatitis; and poultry (chicken, turkeys, quail, pigeons, ornamental birds and others); mycoplasmosis, *E. coli* infections, chronic respiratory tract diseases, salmonellosis, pasteurellosis and psittacosis.

Bacterial diseases can also be treated in the breeding and rearing of stock and ornamental fish, the antibacterial spectrum being extended beyond the abovementioned pathogens to other pathogens, such as, for example, Pasteurella, Brucella, Campylobacter, Listeria, Erysipelothrix, Corynebacteria, Borellia, Treponema, Nocardia, Rickettsia and Yersinia.

The present invention includes pharmaceutical formulations which contain, in addition to non-toxic, inert pharmaceutically suitable excipients, one or more compounds according to the invention or which consist of one or more active compounds according to the invention, and processes for the preparation of these formulations.

The present invention also includes pharmaceutical formulations in dosage units. This means that the formulations are present in the form of individual parts, for example tablets, dragees, capsules, pills, suppositories and ampoules, the active compound contents of which corresponds to a fraction or a multiple of an individual dose. The dosage units can contain, for example, 1, 2, 3 or 4 individual doses or $\frac{1}{2}$, $\frac{1}{3}$ or $\frac{1}{4}$ of an individual dose. An individual dose preferably contains the amound of active compound which is given in one administration and which usually corresponds to a whole, one half, one third or one quarter of a daily dose.

Non-toxic, inert pharmaceutically suitable excipients are to be understood as solid, semi-solid or liquid diluents, fillers and formulation auxiliaries of all types.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds in addition to the customary excipients, such as (a) fillers and extenders, for example starches, lactose, sucrose, glucose, mannitol and silicic acid, (b) binders, for example carbonxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin and (f) absorption accelerators, for example quaternary ammonium compounds, (g) wetting agents, for example cetyl alcohol and glycerol monostearate, (h) absorbents, for example kaolin and bentonite, and (i) lubricants, for example talc, calcium stearate, magnesium stearate and solid polyethylene glycols, or mixtures of the substances listed under (a) to (i).

The tablets, dragees, capsules, pills and granules can be provided with the customary coatings and shells, if appropriate containing opacifying agents, and can also be of such composition that they release the active compound or compounds only or preferentially in a certain part of the intestinal tract, if appropriate in a delayed manner, examples of embedding compositions which can be used being polymeric substances and waxes.

The active compound or compounds can also be in microencapsulated form, if appropriate with one or more of the abovementioned excipients.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid) or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethylene glycols, silicones, bentonites, silicic acid, talc and zinc oxide, or mixtures of these substances.

Powders and sprays can contain, in addition to the active compound or compounds, the customary excipients, for example lactose, talc, silicic acid, aluminium hydroxide, calcium silicate and polyamide powder, or mixtures of these substances. Sprays can additionally contain the customary propellants, for example chlorofluorohydrocarbons.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, maize germ oil, olive oil, castor oil and sesame oil, glycerol, glycerol format, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol and propylene glycol, and suspending agents, for example ethoxylated isostearyl alcohols, polyoxyethylene sorbital and sorbitan esters, microcrystalline cellulose, aluminium metahydroxide, bentonite, agar-agar and tragacanth, or mixtures of these substances.

The formulation forms mentioned can also contain colouring agents, preservatives and smell- and taste-improving additives, for example peppermint oil and eucalyptus oil, and sweeteners, for example saccharin.

The therapeutically active compounds should preferably be present in the abovementioned pharmaceutical formulations in a concentration of about 0.1 to 99.5, preferably about 0.5 to 95% by weight of the total mixture.

The abovementioned pharmaceutical formulations can also contain other pharmeceutical active compounds, in addition to the compounds according to the invention.

The abovementioned pharmaceutical formulations are prepared in the customary manner by known methods, for example by mixing the active compound or compounds with the excipient or excipients.

The formulations mentioned can be used on humans and animals either orally, rectally, parenterally (intravenously, intramuscularly or subcutaneously), intracisternally, intravaginally, intraperitoneally or locally (powder, ointment and drops) and for the therapy of infections in hollow spaces and body cavities. Suitable formulations are injection solutions, solutions and suspensions for oral therapy, gels, infusion formulations, emulsions, ointments or drops. Opthalmological and dermatological formulations, silver salts and other salts, ear drops, eye ointments, powders or solutions can be used for local therapy. In the case of animals, intake can also be via the feed or drinking water in suitable formulations. It is furthermore possible to use gels, powders, dusts, tablets, sustained release tablets, premixes, concentrates, granules, pellets, tablets, boli, capsules, aerosols, sprays and inhalates on humans and animals. The compounds according to the invention can furthermore be incorporated into other carrier materials, such as, for example, plastics (chains of plastic for local therapy), collagen or bone cement.

In general, it has proved advantageous both in human medicine and in veterinary medicine to administer the active compound or compounds according to the invention in total amounts of about 0.5 to about 500, preferably 5 to 100 mg/kg of body weight every 24 hours, if appropriate in the form of several individual doses, to achieve the desired results. An individual dose preferably contains the active compound or compounds in amounts of about 1 to about 80, in particular 3 to 30 mg/kg of body weight. However, it may be necessary to deviate from the dosages mentioned, and in particular to do so as a function of the nature and body weight of the subject to be treated, the nature and severity of the disease, the nature of the formulation and of the administration of the medicament and the period or interval within which administration takes place.

Thus it can in some cases be sufficient to manage with less than the abovementioned amount of active compound, whilst in other cases the abovementioned amount of active compound must be exceeded. The particular optimum dosage required and mode of administration of the active compounds can easily be specified by any expert on the basis of his expert knowledge.

The new compounds can be administered in the customary concentrations and formulations together with the feed or with feed formulations or with the drinking water. An infection by Gram-negative or Gram-positive bacteria can thereby be prevented, improved and/or cured and a promotion in growth and an improvement in feed utilization can thereby be achieved.

The table below shows a comparison of the MIC values of 3S-9-fluoro-2,3-dihydro-3-methyl-10(4-methyl-1-piperazinyl)-7-oxo-7H-pyrido[1,2,3-de][1,4]-benzoxazine-6-carboxylic acid with those of the corresponding racemate (ofloxacin).

| MIC (mcg/ml) E. coli | Example 4 | Example 16 | Ofloxacin |
| --- | --- | --- | --- |
| 4418 | 0.125 | 2 | 0.25 |
| T 7 | 0.03 | 1 | 0.06 |
| A 261 | ≦0.015 | 0.25 | 0.03 |
| Klebsiella 63 | 0.06 | 2 | 0.125 |
| 57 USA | 0.125 | 4 | 0.25 |
| 6318 | 0.125 | 4 | 0.25 |
| Proteus 1875 | 0.06 | 4 | 0.125 |
| Vulg. 1017 | 0.06 | 2 | 0.125 |
| Providencia 12012 | 0.06 | 4 | 0.25 |
| Staph. F 422 | 0.25 | 16 | 0.5 |
| 1756 | 0.25 | 8 | 0.5 |
| 133 | 0.25 | 8 | 0.5 |
| Strepto 9790 | 1 | 32 | 2 |
| Pseudomonas Walter | 1 | 32 | 2 |
| Ellsworth | 0.25 | 4 | 0.5 |

Agar dilution test (isosensitest medium); Denley multipoint inoculator

The following examples illustrate the invention:

EXAMPLE 1

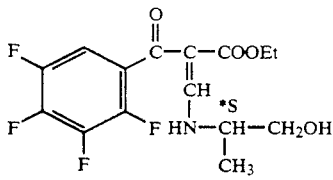

8 g of 3-ethoxy-2-(2,3,4,5-tetrafluorobenzoyl)acrylic acid ethylester are taken in 10 ml of ethanol. 2.1 g of S-(+)-2-aminopropanol in 10 ml of EtOH are added dropwise, while cooling with ice. The mixture is stirred at room temperature for 2 hours and then concentrated in vacuo. 9.5 (crude) of the title compound remain.

EXAMPLE 2

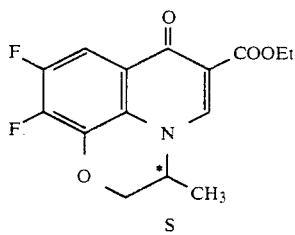

9.5 g of the crude product from Example 1 are heated at 140° C. with 4.3 g of $K_2CO_3$ in 40 ml of dimethylformamide for 4 hours. After the mixture has been cooled to room temperature, water is added and the solid which has precipitated out is isolated. Yield: 5.7 g of ethyl 3S-9,10-difluoro-3-methyl-7-oxo-7H-pyrido[1,2,3-de][1,4]-benzoxazine-6-carboxylate. Melting point: 238–°42° C.

EXAMPLE 3

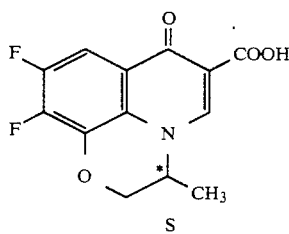

5.7 g of the product from Example 2 are heated at 150° C. (bath) together with 21 ml of acetic acid, 16 ml of water and 1.8 ml of sulphuric acid for 4 hours. After the mixture has been cooled and water has been added, 4.6 g of 3S-9,10-difluoro-3-methyl-7-oxo-7H-pyrido[1,2,3-de][1,4]-benzoxazine-6-carboxylic acid are obtained. Melting point: >300° C.

EXAMPLE 4

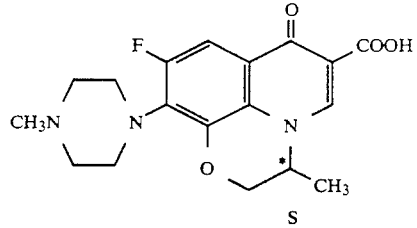

4.6 g of the product from Example 3 and 5.1 g of N-methyl-piperazine are heated at 140° C. in 50 ml of dimethylsulphoxide for 2.5 hours. Thereafter, the dimethylsulphoxide is stripped off under a high vacuum. The residue which remains is boiled up the EtOH and the solid which has precipitated out is isolated. Yield: 2.0 g of 3S-9-fluoro-3-methyl-10(4-methyl-1-piperazinyl)-7-oxo-7H-pyrido[1,2,3-de][1,4]-benzoxazine-6-carboxylic acid.

After recrystallization from dimethylformamide, the compound has a melting point of 298°–°300° C. (decomposition).

$[\alpha_D^{20} = 55.5°$ (C=0.18 In HCL).

EXAMPLE 5

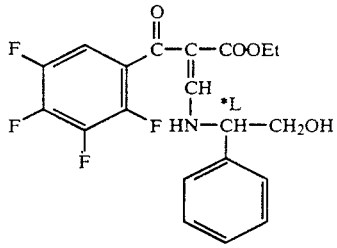

6.4 g of ethyl 3-ethoxy-2-(2,3,4,5-tetrafluorobenzyl)-acrylate are taken in 8 ml of ethanol. A solution of 3 g of L(+)-α-phenylglycinol in 15 ml of ethanol is added dropwise, while cooling. The mixture is subsequently stirred at room temperature for 3 hours and then concentrated.

Yield: 9.2 g of the title compound as an oil.

EXAMPLE 6

The ethoxyacrylic ester is reacted with [-(−)α-phenylglycinol analogously to Example 5. Yield: 9.2 g of oil.

EXAMPLE 7

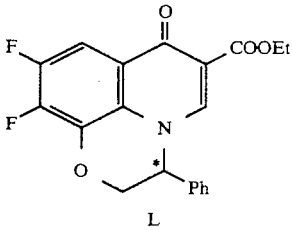

9.2 g of the product from Example 5 are heated at 140° C. with 3.3 g of potassium carbonate in 40 ml of dimethylformamide for 4 hours. After cooling to room temperature, the mixture is diluted with water and the solid is isolated. After drying, the product is stirred with a little methanol.

Yield 5 g of ethyl 3L-9,10-difluoro-3-phenyl-7-oxo-7H-pyrido[1,2,3-de][1,4]-benzoxazine-6-carboxylate Melting point: >300° C.

EXAMPLE 8

3.3 g of ethyl 3D-9,10-difluoro-3-phenyl-7-oxo-7H-pyrido-[1,2,3-de][1,4]-benzoxazine-6-carboxylate are obtained analogously to Example 7 from 9.4 g of the product from Example 6.

Melting point: >300° C.

EXAMPLE 9

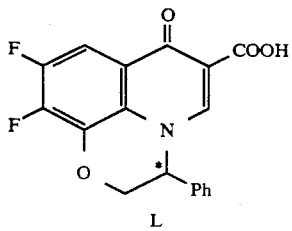

4 g of the product from Example 7 are boiled together with 13 ml of acetic acid, 12 ml of water and 1.2 ml of sulphuric acid for 6 hours. Thereafter, water is added and the solid which has precipitated out is isolated.

Yield: 3.3 g of 3L-9,10-difluoro-3-phenyl-7-oxo-7H-pyrido[1,2,3-de][1,4]-benzoxazine-6-carboxylic acid Melting point: 181-°82° C.

EXAMPLE 10

2.0 g of 3D-9,10-difluoro-3-phenyl-7-oxo-7H-pyrido[1,2,3-de][1,4]-benzoxazine-6-carboxylic acid are obtained analogously to Example 9 from 2.2 g of the precursor from Example 8.

EXAMPLE 11

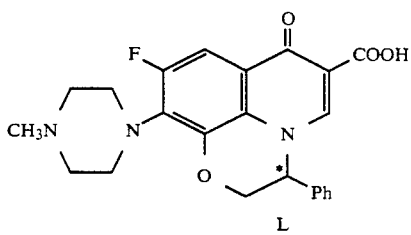

2.8 g of the product from Example 9 and 4 g of N-methyl-pioerazine are heated at 140° C. in 25 ml of dimethylsulphoxide for 2.5 hours. Thereafter, all the volatile consitiuents are distilled off under a high vacuum.

The residue is stirred with water and the solid obtained is isolated.

Yield: 2.6 g of 3L-9-fluoro-10(4-methyl-1-piperazinyl)-3-phenyl-7-oxo-7H-pyrido[1,2,3-de][1,4]-benzoxazine-6-carboxylic acid.

Melting point: 252-°3° (decomposition).

EXAMPLE 12

1.4 g of 3D-9-fluoro-10(4-methyl-1-piperazinyl)-3-phenyl-7-oxo-7H-pyrido[1,2,3-de][1,4]-benzoxazine-6-carboxylic acid are obtained analogously to Example 11 from 1.5 g of the precursor from Example 10. Melting point 257° C. (decomposition).

EXAMPLE 13

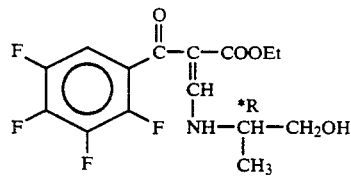

5.76 g of ethyl 3-ethoxy-2-(2,3,4,5-tetrafluorobenzoyl)-acrylate are taken in 10 ml of ethanol. 1.5 g of R-(−)-2-amino-propanol in 10 ml of ethanol are added dropwise, while cooling with ice. The mixture is stirred at room temperature for 2 hours and then concentrated in vacuo. 6.8 g (crude) of the title compound remain.

EXAMPLE 14

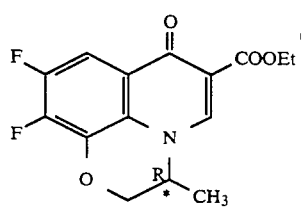

6.8 g of the crude product from Example 13 are heated at 140° C. with 3 g of potassium carbonate in 30 ml of dimethylformamide for 4 hours. After the mixture has been cooled to room temperature, water is added and the solid which has precipitated is isolated.

Yield: 4.2 g of ethyl 3R-9,10-difluoro-3-methyl-7-oxo-7H-pyrido[1,2,3-de][1,4]-benzoxazine-6-carboxylate.

Melting point: 236-°238° C.

EXAMPLE 15

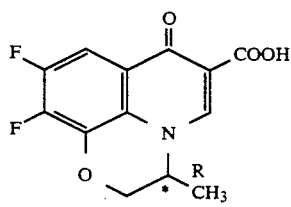

4.0 g of the product from Example 14 are heated at 140° C. together with 15 ml of acetic acid, 11 ml of water and 1.3 ml of sulphuric acid for 4 hours. After cooling and adding water, 3.5 g of 3R-9,10-difluoro-3-methyl-7-oxo-7H-pyrido[1,2,3-de][1,4]-benzoxazine-6-carboxylic acid are obtained.

Melting point: >300° C.

EXAMPLE 16

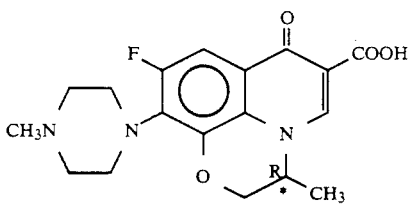

3.5 g of the product from Example 15 and 3.9 g of N-methylpiperazine are heated at 140° C. in 30 ml of dimethylsulphoxide for 2.5 hours. Thereafter, all the volatile constituents are stripped off under a high vacuum. EtOH is added to the residue which remains. The solid which has precipitated is isolated and recrystallized from dimethylformamide.

Yield: 2.0 g of 3R-9-fluoro-3-methyl-10(4-methyl-1-piperazinyl)-7-oxo-7H-pyrido[1,2,3-de][1,4]-benzoxazine-6-carboxylic acid.

Melting point: 295°–298° C. (decomposition)

$[\alpha]_D^{20} = +53.8°$ (C=0.18 1n HCl.

It will be understood that the specifications and examples are illustrative but not limitative of the present invention and that other embodiments within the spirit and scope of the invention will suggest themselves to those skilled in the art.

What is claimed is:

1. A process for the preparation of an enantiomerically pure 1,8-bridged 4-quinolone-3-carboxylic acid and derivatives thereof of the formula

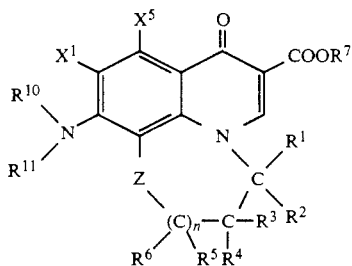

wherein $R^7$ represents $C_1$-$C_4$-alkyl and $R^8$ and $R^9$ represent hydrogen or $C_1$-$C_4$-alkyl, and $R^9$ can also be optionally substituted phenyl, $X^1$ represents hydrogen, nitro, alkyl with 1 to 3 carbon atoms or halogen, $R^5$ represents hydrogen, halogen or methyl, $R^{10}$ and $R^{11}$, together with the nitrogen atom to which they are bonded, form a 5- or 6-membered heterocyclic ring which can additionally contain, as a ring member, the atoms or groups —O—, —S—, —SO—, —SO$_2$—,

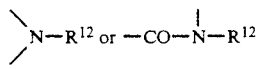

and which can optionally be mono-, di- or trisubstituted on the carbon atoms by $C_1$-$C_4$-alkyl, by phenyl or cyclohexyl which is optionally mono-, di- or trisubstituted by chlorine, fluorine, bromine, methyl, phenyl, hydroxyl, methoxy, benzyloxy, nitro or piperidino, or by 2-thienyl, hydroxyl, alkoxy with 1 to 3 carbon atoms, amino, methylamino or ethylamino, aminomethyl, methylaminomethyl or ethylaminomethyl, wherein $R^{12}$ represents hydrogen or a branched or straight-chain alkyl, alkenyl or alkinyl group which has 1 to 6 carbon atoms and can optionally be substituted by one or two hydroxyl, alkoxy, alkylamino or dialkylamino groups with 1 to 3 carbon atoms for an alkyl radical, the cyano group or the alkoxycarbonyl group with 1 to 4 carbon atoms in the alkoxy part, or represents a phenylalkyl group which has up to 4 carbon atoms in the aliphatic part and is optionally substituted in the phenyl radical, a phenacyl radical which is optionally mono- or disubstituted by hydroxyl, methoxy, chlorine or fluorine, or an oxoalkyl radical with up to 6 carbon atoms, or furthermore denotes a radical $COR^{13}$ or $SO_2R^{14}$, wherein $R^{13}$ represents hydrogen or straight-chain or branched alkyl which has 1 to 4 carbon atoms and is optionally substituted by 1 or 2 substituents from the series comprising amino, alkoxycarbonyl with 1 to 3 carbon atoms in the alkoxy part, carboxyl, alkoxy with 1 to 3 carbon atoms and halogen, or represents alkoxy with 1 to 4 carbon atoms, amino or alkylamino or dialkylamino with 1 to 5 carbon atoms in the alkyl part and $R^{14}$ represents straight-chain or branched alkyl with 1 to 3 carbon atoms, and Z represents oxygen or an amine radical $NR^{15}$, wherein $R^{15}$ denotes hydrogen or an alkyl radical which has 1–6 carbon atoms and is optionally substituted by halogen, trifluoromethyl, nitro, cyano, hydroxyl, alkoxy or alkylmercapto with 1–3 carbon atoms, aryloxy, arylthio or an ester radical with 1–3 carbon atoms in the alkoxy part, or denotes a phenyl radical which is optionally substituted by halogen, a nitro group, an alkyl group with 1–3 carbon atoms or an alkoxy or alkylmercapto group with in each case 1–3 carbon atoms, or furthermore represents an acyl radical $R^{16}$—CO— or $R^{17}SO_2$—, wherein $R^{16}$ and $R^{17}$ represent alkyl radicals with 1–6 carbon atoms or optionally substituted phenyl radicals, or can be a

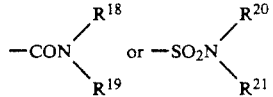

radical, wherein the radicals $R^{18}$ to $R^{21}$ represent hydrogen, alkyl with 1–6 carbon atoms or an optionally substituted phenyl radical, and $R^1$, $R^2$, $R^3$, $R^4$, $R^5$ and $R^6$ represent hydrogen or an alkyl group which has 1–6 carbon atoms and is optionally mono- or polysubstituted by halogen, and furthermore nitro, cyano, hydroxyl, alkoxy or alkylmercapto with 1–3 carbon atoms in the alkyl part, or represent a phenyl radical, naphthyl radical or heterocyclic radical which is optionally substituted by halogen, nitro, alkyl or alkoxy or alkylmercapto with in each case up to 3 carbon atoms, hydroxyl, aryloxy arylthio cyano or an ester radical with 1-3 carbon atoms in the alcohol part, with the proviso that $R^1$ and $R^2$ and/or $R^3$ and $R^4$ and/or $R^5$ and $R^6$ are different, and $R^2$ with $R^3$ and/or $R^4$ with $R^5$, can in each case with the carbon atoms to which they are bonded, form a 3- to 7-membered ring which is optionally substituted by optionally substituted alkyl radicals with 1-3 carbon atoms or optionally substituted aryl radicals and n denotes 0 or 1 comprising 1) reacting a compound of the formula

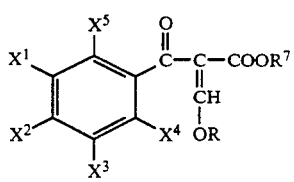

wherein $X_2 = F$ or Cl, $X^3 = X^4 = F$, Cl or $NO_2$ and $R = CH_3$, $C_2H_5$ or $C_7H_7$—n with a compound of the formula

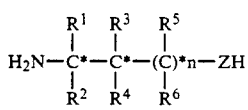

to form a compound of the formula

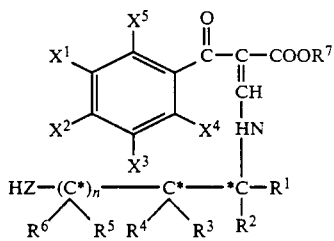

2) cyclizing the product of step 1) to form a compound of the formula

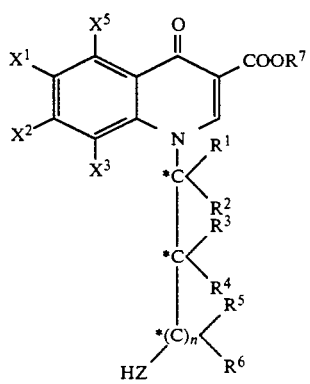

3) cyclizing the product of step 2) to form a compound of the formula

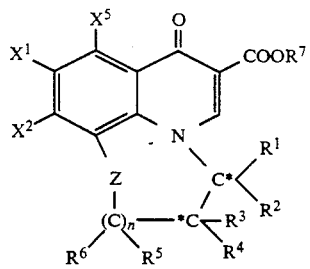

and 4) reacting the product of step 3) with an amine of the formula

2. A process for the preparation of an enantiomerically pure 1,8-bridged 4-quinolone-3-carboxylic acid and derivatives thereof according to claim 1, wherein a 10-(1-piperazinyl) compound (with n=o) or 11-(1-piperazinyl) compound (with n=1) of the formula

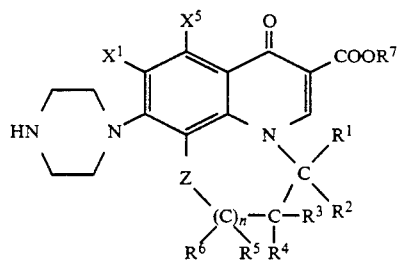

in which
the piperazinyl radical can be mono-, di- or tri-substituted on the carbon atoms by $C_1$-$C_4$-alkyl, 2-thienyl or optionally substituted cyclohexyl or phenyl, is reacted with a compound of the formula $R^{12}X$ 

in which
$R^{12}$ has the abovementioned meaning, but cannot be hydrogen, and
X denotes fluorine, chlorine, bromine, iodine, hydroxyl, acyloxy, ethoxy, phenoxy or 4-nitrophenoxy.

3. A process according to claim 1, in which
Y represents a carboxyl group, a nitrile group or an ester group —$COOR^7$, wherein
$R^7$ can be methyl or ethyl,
$X^1$ represents fluorine,
$X^5$ represents hydrogen,
$R^{10}$ and $R^{11}$, together with the nitrogen atom to which they are bonded, can form a 5- or 6-membered heterocyclic ring which can additionally contain, as a ring member, an oxygen atom or the groups

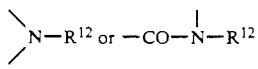

and which can optionally be mono-, di- or trisubstituted on the carbon atoms by $C_1$-$C_2$-alkyl, cyclohexyl or phenyl which is optionally substituted by chlorine, fluorine, methyl, phenyl, hydroxyl, methoxy, benzoyloxy, nitro or piperidino, or by 2-thienyl or hydroxyl, wherein $R^{12}$ represents hydrogen or a branched or straight-chain alkyl group with has 1 to 3 carbon atoms and can optionally be substituted by one or two hydroxyl groups, or represents a phenacyl radical, or an oxalkyl radical with up to 4 atoms, or a radical $COR^{13}$, wherein $R^{13}$ denotes hydrogen or alkyl with one or two carbon atoms, Z represents oxygen or an amine radical $NR^{15}$, wherein $R^{15}$ represents an alkyl radical with 1–4 carbon atoms or represents a phenyl radical which is optionally substituted by halogen, methyl or nitro.

* * * * *

UNITED STATES PATENT AND TRADEMARK OFFICE
CERTIFICATE OF CORRECTION

PATENT NO. : 5,237,060
DATED : August 17, 1993
INVENTOR(S) : Schriewer, et al.

It is certified that error appears in the above-indentified patent and that said Letters Patent is hereby corrected as shown below:

| | |
|---|---|
| Col. 1, line 63 | Delete " thee " and substitute -- the -- |
| Col. 23, line 52 | Delete " $R^5$ " and substitute -- $X^5$ -- |
| Col. 24, line 3 | Delete " or " and substitute -- , -- |
| Col. 24, lines 9-10 | Delete " for an " and substitute -- in each -- |

Signed and Sealed this

Ninth Day of May, 1995

Attest:

BRUCE LEHMAN

*Attesting Officer*     *Commissioner of Patents and Trademarks*